United States Patent [19]

Courty

[11] 4,199,436
[45] Apr. 22, 1980

[54] PROCESS FOR STEAM-DEALKYLATING ALKYLAROMATIC HYDROCARBONS

[75] Inventor: Philippe Courty, Houilles, France

[73] Assignee: Institut Francais du Petrole, Rueil-Malmaison, France

[21] Appl. No.: 11,608

[22] Filed: Feb. 12, 1979

[51] Int. Cl.² .................. C07C 3/58; C07C 15/06; C10G 39/00; B01J 23/64

[52] U.S. Cl. .................. 208/124; 208/62; 208/112; 208/138; 252/466 PT; 423/652; 585/487

[58] Field of Search ............ 208/62, 112, 124, 138; 252/466 PT; 423/652; 585/487

[56] References Cited

U.S. PATENT DOCUMENTS

| | | | |
|---|---|---|---|
| 3,436,433 | 4/1969 | Lester | 585/487 |
| 3,449,078 | 10/1969 | Quik et al. | 423/654 |
| 3,562,346 | 2/1971 | Smirnov et al. | 208/138 X |
| 3,595,932 | 7/1971 | Maslyansky et al. | 585/487 |
| 3,617,518 | 11/1971 | Sinfelt | 208/138 |
| 3,649,706 | 3/1972 | Lester | 585/487 |
| 3,649,707 | 3/1972 | Lester | 208/74 X |
| 3,650,944 | 3/1972 | McCoy et al. | 208/65 |
| 3,729,408 | 4/1973 | Carter et al. | 252/474 X |
| 4,013,734 | 3/1977 | Kim | 585/487 |

FOREIGN PATENT DOCUMENTS

| | | | |
|---|---|---|---|
| 2139043 | 2/1972 | Fed. Rep. of Germany | 208/124 |
| 213776 | 2/1971 | U.S.S.R. | 208/124 |

Primary Examiner—Delbert E. Gantz
Assistant Examiner—G. E. Schmitkons
Attorney, Agent, or Firm—Millen & White

[57] ABSTRACT

Alkylaromatic hydrocarbons are steam-dealkylated in the presence of a catalyst comprising an alumina carrier and 0.1 to 2% b.w. of a group VIII noble metal, 0.05 to 2% of a group $I_B$ metal and 0.01 to 5% of an alkali metal.

10 Claims, No Drawings

PROCESS FOR STEAM-DEALKYLATING ALKYLAROMATIC HYDROCARBONS

BACKGROUND OF THE INVENTION

This invention relates to steam dealkylation reactions for producing benzene or its lower homologs by dealkylation of toluene and other alkylbenzenes.

A number of catalysts have been proposed for steam-dealkylating aromatic hydrocarbons, which catalysts comprise a porous carrier and at least one metal deposited on the carrier. By way of examples, there can be mentioned:

U.S.S.R. Pat. No. 213,776, wherein the catalyst comprises rhodium, nickel and alumina;

U.S. Pat. No. 3,595,932, wherein the catalyst comprises a noble metal of the platinum family (platinum, palladium, rhodium, iridium, ruthenium) on a carrier consisting of alumina or combinations of alumina with nickel or cobalt;

U.S. Pat. No. 3,436,433, wherein the catalyst comprises alumina, an alkali metal, ferric oxide, rhodium and chromium;

U.S. Pat. No. 3,649,706 and 3,649,707, wherein the catalysts comprise mixtures of an alkali metal with ferric oxide, chromium and a metal selected from platinum, palladium and rhodium;

U.S. Pat. No. 4,013,734, wherein the catalyst comprises alumina, a noble metal of the platinum family and a metal selected from vanadium, niobium and tantalum;

French Pat. No. 2,317,962, wherein the catalyst comprises alumina or aluminosilicates in addition to rhodium and a metal from group IV A, particularly tin.

The catalysts used up to now yield fairly good results as concerns activity, but, on the one hand, their stability is insufficient and, on the other hand, their selectivity is not high enough; in addition to the conversion of the alkylaromatics to benzene, parasitic reactions of hydrocracking or steam-cracking of the aromatic ring take place, which lead to undesirable gaseous products such as CO, $CO_2$ and $CH_4$, and reduce both the hydrogen and aromatics yields.

OBJECTS OF THE INVENTION

The present invention has for object to obviate these major disadvantages by providing a process whereby the yield of final product may be increased by the selection of selective and stable catalysts.

DETAILED DISCUSSION

This object is achieved by manufacturing benzene and/or its lower homologs by dealkylation of alkyl benzenes (toluene, xylenes, etc...) by steam conversion in the presence of specific catalysts.

The operating temperature is generally from 300 to 600° C., preferably from 350 to 550° C. and the pressure is from 1 to 20 atmospheres and preferably from 3 to 10 atmospheres, while the LHSV (Liquid Hourly Space Velocity) i.e. a liquid VVH (space velocity) is from 0.1 to 10 volumes of hydrocarbons per volume of catalyst and per hour, preferably from 1 to 5, the ratio (by moles) of $H_2O$ to the hydrocarbons being from 1 to 20, preferably from 3 to 15.

The process yields both total dealkylation products, such as benzene, and partial dealkylation products such as, for example, toluene from xylenes.

More precisely, the process yields benzene, toluene, xylenes, ethylbenzene with substantial hydrogen amounts. According to the process, it is possible, for example, to dealkylate toluene, xylenes, ethylbenzene, propylbenzene, or hydrocarbons with condensed rings such as naphthalene, phenanthrene, anthracene, etc . . . There can also be mentioned mesitylene, pseudocumene, hemimellitene; according to the process, such hydrocarbons as alkylcyclohexanes, alkyltetralines, alkyldecalines and alkyldihydroanthracenes may be aromatized and dealkylated thereafter.

According to the process, aromatic nitrogen compounds, for example pyridine derivatives, may also be dealkylated, nitrogen being eliminated as $NH_3$ or $N_2$.

The process is of particular efficiency for dealkylating alkyl aromatic hydrocarbons recovered from catalytic reforming reactions or reactions for producing aromatic hydrocarbons ("Aromizing").

The catalysts, according to the invention, give high yields of dealkylated hydrocarbons (for example high benzene yields) with simultaneous low degradation of the aromatic ring. They yield a reaction gas of high hydrogen content (from about 50 to about 70% by volume of hydrogen) which can be easily marketed. They also exhibit a high stability under the most severe conditions.

The specific catalysts to be used in the present invention comprise:
(a) a carrier consisting essentially of alumina whose specific surface is preferably higher than 50 $m^2/g$, more particularly higher than 80 $m^2/g$, and, by weight:
(b) 0.1 to 2% of at least one noble metal from group VIII of the periodic classification, selected from ruthenium, rhodium, palladium, osmium, iridium and platinum,
(c) 0.05 to 2% of at least one metal from group $I_B$ selected from copper, silver and gold, copper and silver being the preferred metals,
(d) 0.01 to 5% of at least one alkali metal (group $I_A$) selected from lithium, sodium, potassium, rubidium and cesium. Potassium is the preferred metal.

Preferred catalysts comprise at least two noble metals from group VIII, for example (by weight):
0.1 to 1% of rhodium
0.2 to 1.5% of another noble metal from group VIII, preferably ruthenium or palladium or platinum. Rhodium amounts to about 20 to 80% by weight of all the metals of group VIII in said catalyst.

Another preferred catalyst comprises (by weight):
0.25 to 0.65% of rhodium,
0.1 to 0.9% of copper and
0.5 to 3% of potassium.

A further preferred catalyst comprises (by weight):
0.2 to 0.65% of rhodium, 0.10 to 0.90% of at least one noble metal selected from the group consisting of ruthenium, palladium and platinum,
0.1 to 1.9% of copper and
0.5 to 3% of potassium.

The catalyst carrier according to the invention is preferably selected from eta-cubic $\eta$, gamma-cubic $\gamma_C$, gamma tetragonaly $\gamma_T$, khi cubic $\chi$, kappa-orthorhombic k, theta-monoclinic $\theta$, delta-orthorombic $\delta$ and rho-amorphous $\rho$ aluminas.

It has a specific surface from 50 to 400 m²/g and preferably from 80 to 350 m²/g and a total pore volume from 30 to 150 ml/100 g.

The method of manufacture of the catalysts is not a critical feature of the invention and any known method may be used. The active elements are supplied either simultaneously or separately to the carrier by impregnation with aqueous solutions, or solutions, in an appropriate solvent, of soluble salts of the above active elements.

The impregnations may be effected either in the dry state, by filling the pore volume of the carrier with the same volume of impregnation solution and then, after optional ageing, drying said carrier; or with an excess of solution, by contacting the carrier with a volume of solution higher than the pore volume of said carrier and waiting for sufficient time to let the metal ions of the solution settle on the carrier by exchange reaction.

The following soluble salts of the above metals may be mentioned: the halides, nitrates, acetates, basic carbonates, formates, oxalates, citrates, the chlorometallic acids and their ammonium and amine salts, the complexes comprising at least one of the above metals with oxalic acid and the oxalates, citric acid and the citrates, tartaric acid and the tartrates, with other poly-acids, acid-alcohols, amina-alcohols and their salts, the acetylacetonates, etc . . .

A method, taken by way of example, consists of impregnating the carrier with a solution comprising at least one metal of the platinum family (group VIII), then drying it, for example at 100 to 250° C. for at least one hour, then thermally activating it (calcination for at least one hour at about 300 to 600° C. and/or reduction for at least one hour at about 200 to 500° C. in the presence of a gas containing at least 10% by volume of hydrogen), then impregnating the resulting material with a solution containing at least one metal from group $I_B$ (Cu, Ag, Au) and optionally at least one metal from group $I_A$ (Li, Na, K, Rb, Cs), drying and calcining and/or reducing it as above, then finally optionally impregnating it with a solution containing at least one metal from group $I_A$ (Li, Na, K, Rb, Cs), drying and calcining and/or reducing as above.

By way of another example, the carrier may be impregnated with a solution containing at least one metal from group $I_B$ (Cu, Ag, Au) and optionally at least one metal from group $I_A$ (Li, Na, K, Rb, Cs), then drying and calcining are performed at 300° to 700° C. for at least one hour, so as to partially or totally combine the alumina of the carrier with at least one metal from group $I_B$ (Cu, Ag, Au), so as to form a mixed oxide of the aluminate type of the formula $Al_2O_3 nM_mO$ (n=1, 2, 3; m=1, 2; M=Cu, Ag, Au).

The carrier impregnated with the above metals may also be calcined and then reduced for at least one hour at 200° to 500° C., then impregnated with a solution containing at least one metal of the platinum family (group VIII), then dried and activated and/or reduced as above, and finally optionally impregnated with a solution containing at least one metal group $I_A$ (Li, Na, K, Rb, Cs), dried and then calcined and/or reduced as above.

A final example consists of preparing a solution comprising at least one metal from the platinum family (group VIII), at least one metal from the group $I_B$ (Cu, Ag, Au) and at least one metal from the group $I_A$ (Li, Na, K, Rb, Cs), impregnating the carrier with this solution and then drying and calcining and/or reducing it according to the above conditions.

More generally, drying is effected, for example, at about 100° C. and then at about 200° C. for 1 hour or more, and the heat activation is effected at 300° to 600° C. for 1 hour or more, in the presence of nitrogen or an oxygen-containing gas.

Reduction is effected at 200° to 400° C. in the presence of a gas containing at least 10% $H_2$ for one hour or more.

Reduction of the catalyst is preferably effected by passing a hydrogen stream at 100° to 500° C. before any contact with the hydrocarbons to be dealkylated.

The following, non-limitative examples illustrate various aspects of the invention.

These examples concern the manufacture of catalysts accorcing to the invention, and the use thereof for dealkylating toluene in the presence of steam. The user of the catalysts is not limited to this particular hydrocarbon. It is selected to test the activity and selectivity of the catalysts for dealkylation, as it is the case of normal heptane which is used to test the properties of the reforming catalysts, or ethylbenzene for the aromatic hydrocarbons isomerisation catalysts. As pointed out above, the alkylaromatic hydrocarbon feedstocks may be quite diverse.

The manufacture of catalysts A to K is first disclosed; catalyst A and F are no part of the invention.

The performances obtained in the test reaction of dealkylating toluene to benzene are stated in Tables I and II. The toluene conversion and the yields to benzene, xylene and by-products are given in moles %.

The operating conditions of the test are the following:

Feedstock:toluene of 99.85% b.w. purity with 0.16 ppm sulfur.
Pressure:7 atm.
L.H.S.V.:1.5 vol. toluene per volume of catalyst per hour.
$H_2O$/toluene:6 moles/mole
Initial activity measured after 10 hours of run.

Table I shows that the addition of at least one metal $I_B$ (Cu, Ag, Au) to the mixture of at least one noble metal from group VIII (Ru, Rh, Pd, Os, Ir, Pt) with at least one metal from group $I_A$ (Li, Na, K, Rb, Cs), while yielding catalysts of at least identical activity, yields catalysts of higher specificity, i.e. giving a higher benzene yield at a given conversion rate.

(Comparison between catalysts A and B, on the one hand, and E and F, on the other hand).

Table II shows that the catalysts conforming to the invention (for example, catalyst B) have higher stability versus time than the reference catalysts (for example, catalyst A), while being largely more specific.

EXAMPLE 1 (comparison example)

The carrier consists of γC and γT alumina in the form of extrudates of 1.2 mm diameter and 5 to 7 mm length having a specific surface 260 m²/g and a total pore volume of 58 ml/100 g, previously moistened by steaming at 80° C. (water vapor pressure=saturation pressure).

100 g of this carrier is immersed into 120 ml of solution containing 0.61 g of rhodium as rhodium trichloride and 4 ml of pure hydrochloric acid ($d_{20°}$ C.=1.19).

After exhaustion of the solution (rhodium cannot be detected by adding stannous chloride to the solution: the presence of rhodium would give a characteristic red coloration), the catalyst is filtered, dried for 2 hours at 100° C., 2 hours at 200° C. and then activated in air at 400° C. for 2 hours.

The carrier is finally impregnated with 1.1% potassium in the form of 55 ml of an aqueous solution of potassium nitrate, then dried for 2 hours at 100° C. and for 1 hour at 200° C., and reduced with $H_2$ for 2 hours at 300° C. Resultant caralyst A contains 0.6% Rh and 1% K (by weight).

EXAMPLE 2

100 g of the carrier from example 1 is contacted with 120 ml of solution containing 0.41 g copper as copper chloride and 0.5 ml pure hydrochloric acid ($d_{20°C.}=1.19$). After 3 hours, copper was totally exchanged on the carrier; the latter is filtered, dried for 1 hour at 100° and 2 hours at 150° C. and activated in air for 5 hours at 400° C. The catalyst is then impregnated with 55 ml of a solution comprising 0.61 g of rhodium as trichloride, 1.1 g of potassium as nitrate, 1.5 g of citric acid monohydrate and 2 ml of pure hydrochloric acid ($d_{20°C.}=1.19$). After ageing for 4 hours at 20° C., the catalyst is dried at 120° C. for 10 hours, then activated in air at 400° C. for 1 hour and finally reduced at 350° C. for 2 hours in the presence of a gas containing 0.8 vol. $N_2$ per 0.2 vol. $H_2$.

The resulting catalyst (catalyst B) contains 0.4% Cu, 0.6% Rh and 1% K (by weight).

EXAMPLE 3

The preparation of example 1 is repeated, while adding 0.61 g of silver nitrate to the aqueous solution of potassium nitrate; the resulting catalyst (catalyst C) comprises 0.6% Rh, 0.6% Ag and 1% K by weight.

EXAMPLE 4

The preparation of example 1 is repeated, while adding 0.92 g of gold, in the form of chloroauric acid, to the aqueous solution of potassium nitrate, the total volume of the solution remains 55 ml. The impregnated catalyst is dried as above, than activated in air at 430° C. for 2 hours and finally reduced at 500° C. for 1 hour in the presence of a nitrogen-hydrogen mixture (0.8 $N_2$ per 0.2 $H_2$ by volume).

The resulting catalyst (catalyst D) comprises 0.6% Rh, 0.9% Au and 1% K by weight.

EXAMPLE 5

There is used a $Y_C$ carrier of the trade consisting of balls of diameters between 0.8 and 1.5 mm having a specific surface of 240 m²/g and a total pore volume of 55 ml/100 g, previously moistened by steaming at 60° C. (water vapor pressure=saturation pressure).

100 g of this carrier is immersed in 100 ml of solution containing 0.32 g of rhodium (as trichloride), 0.42 g of palladium (as chloride) and 4 ml of pure hydrochloric acid ($d_{20°C.}=1.19$). After exhaustion of the solution, it is found that Pd and Rh are homogeneously present in the carrier balls. After draining, the impregnated carrier is dried at 150° C. for 4 hours, and then reduced directly in the presence of hydrogen. The reduced catalyst is then impregnated with 50 ml of an aqueous solution comprising 0.61 g of copper as chloride, 1 g of citric acid monohydrate and 1.6 g of potassium as nitrate. After 3 hours ageing and 2 hours drying at 150° C., the catalyst is activated for 2 hours at 400° C.

The resulting catalyst E comprises by weight 0.3% Rh, 0.4% Pd, 0.6% Cu and 1.55% K.

EXAMPLE 6

Example 5 is repeated, except that copper is no more used.

Resultant catalyst F comprises by weight 0.3% Rh, 0.4% Pd and 1.55% K.

EXAMPLE 7

The carrier is that described in example 5.

100 g of the carrier previously steamed at 60° C. are immersed in 120 ml of a solution containing 0.42 g of rhodium (as trichloride), 0.42 g of platinum (as chloroplatinic acid) and 5 ml of pure hydrochloric acid ($d_{20°C.}=1.19$). After exhaustion of the solution, it is found that Pt and Rh are homogeneously present in the carrier balls. After draining, the latter are dried for 1 hour at 100° C. and 2 hours at 200° C. and finally calcined at 400° C. for 2 hours. The catalyst is then impregnated with 50 ml of a solution of 0.53 g of copper, 0.11 g of silver and 1.6 g of potassium as nitrates. After ageing for 3 hours in air and a 2 hours drying at 150° C., the catalyst is activated at 400° C. for 2 hours and then reduced in hydrogen at 350° C. for 2 hours.

Resultant catalyst G contains 0.4% Rh, 0.4% Pt, 0.5% Cu, 0.1% Ag and 1.55% K, by weight.

EXAMPLE 8

The carrier is as described in example 5.

100 g of carrier are steamed at 70° C. and then impregnated in the dry state with 54.5 ml of a solution comprising 0.31 g Rh ($RhCl_3$), 0.41 g Ru ($RuCl_4$), 0.52 g Cu ($CuCl_2$), 1.60 g K ($KNO_3$), 4 ml HCl (d=1.19) and 5 g citric acid monohydrate.

After ageing for 4 hours, quick drying at 200° C. for 3 hours in an air stream (volume velocity: 2000 volumes of air (NTP) per volume of catalyst per hour), calcination at 370° C. for 2 hours and reduction at 400° C. for 1 hour (dry $H_2$), there is obtained catalyst H which contains 0.3% Rh, 0.4% Ru, 0.5% Cu and 1.55% K by weight.

EXAMPLE 9

A $\gamma_C$ carrier of the trade, in the form of balls of a diameter between 0.8 and 1.5 mm, having a 260 m²/g specific surface and 80 ml/100 g total pore volume, is moistened at 70° C. by steaming (water vapor pressure=saturation pressure) and impregnated as follows:

100 g of carrier are contacted with 160 ml of solution comprising 0.83 g ruthenium and 0.26 g rhodium (as trichlorides), 4 ml HCl (d=1.19), 30 ml ethanol and 5 g citric acid monohydrate. After exhaustion of the solution, it is found that Ru and Rh are homogeneously present in the carrier balls. After draining, there are dried at 100° C. for 1 hour and then 200° C. for 3 hours, calcined at 380° C. for 2 hours and reduced at 400° C. for 5 hours in the presence of nitrogen containing 20% $H_2$ The reduced catalyst is then impregnated with 0.93 g of silver and 1.60 g of potassium as nitrates (volume of solution: 75 ml), aged in air for 1 hour, dried at 200° C. in dry air and activated in nitrogen at 430° C. for 2 hours.

Resultant catalyst J contains 0.8% Ru, 0.25% Rh, 0.9% Ag and 1.55% K by weight.

EXAMPLE 10

Example 9 (catalyst J) is repeated, except that 0.93 g of silver and 1.60 g of potassium, as nitrates, are replaced with 0.62 g copper and 1.60 g potassium, as chlorides. The other conditions of the preparation of drying and heat activation are identical. Resultant catalyst K comprises 0.8% Ru, 0.25% Rh, 0.6% Cu and 1.55% K by weight.

TABLE I

| EXAMPLE No. | CATALYST No. | TEMPERATURE °C. for a molar conversion of 70% | From 100 moles of toluene at the inlet, there is obtained (moles): | | | |
|---|---|---|---|---|---|---|
| | | | TOLUENE | BENZENE | XYLENES | CRACKED AROMATIC RINGS |
| 1 | A | 462 | 30 | 61.6 | 1 | 7.4 |
| 2 | B | 451 | " | 66.5 | 1.5 | 2 |
| 3 | C | 448 | " | 65.8 | 1.2 | 3 |
| 4 | D | 475 | " | 63.7 | 1.5 | 4.8 |
| 5 | E | 512 | " | 66.4 | 1.3 | 2.3 |
| 6 | F | 525 | " | 60.2 | 1.7 | 8.1 |
| 7 | G | 506 | " | 66.8 | 1.2 | 2.0 |
| 8 | H | 528 | " | 65.8 | 1.2 | 3.0 |
| 9 | I | 506 | " | 66.1 | 1.3 | 2.6 |
| 10 | J | 495 | " | 65.9 | 1.6 | 2.5 |

TABLE II

| CATALYST | AGE OF THE CATALYST (Hours) | T° C. | % MOLAR CONVERSION OF TOLUENE | From 100 moles of toluene at the inlet, there is obtained (moles): | | | |
|---|---|---|---|---|---|---|---|
| | | | | TOLUENE | BENZENE | XYLENE | CRACKED AROMATIC RINGS |
| A (example 1) | 10 h | 453 | 60 | 40 | 52.8 | 1.1 | 6.1 |
| | 500 h | 478 | 60.1 | 39.9 | 51.9 | 1.9 | 6.3 |
| | 2000 h | 535 | 59.4 | 40.6 | 50.0 | 2.3 | 7.1 |
| B (example 2) | 10 h | 441 | 60 | 40 | 57.1 | 1.2 | 1.7 |
| | 500 h | 459 | 59.9 | 40.1 | 57.0 | 1.1 | 1.8 |
| | 2000 h | 491 | 60.2 | 39.8 | 57.3 | 1.4 | 1.5 |

What we claim is:

1. A process for steam-dealkylating a feedstock comprising at least one alkylaromatic hydrocarbon, in the presence of a catalyst comprising an alumina carrier and, by weight with respect to the catalyst, 0.1 to 2% of at least one group VIII noble metal, selected from ruthenium, rhodium, palladium, osmium, iridium and platinum, 0.05 to 2% of at least one metal from group $I_B$, selected from copper, silver and gold and 0.01 to 5% of at least one alkali metal selected from lithium, sodium, potassium, rubidium and cesium.

2. A process according to claim 1, wherein the group VIII metal is rhodium and its content is 0.1 to 1% by weight of the catalyst.

3. A process according to claim 2, wherein the catalyst comprises ruthenium in an amount of 0.2 to 1.5% by weight of the catalyst, in addition to rhodium.

4. A process according to claim 2, wherein the catalyst comprises palladium in an amount of 0.2 to 1.5% by weight of the catalyst, in addition to rhodium.

5. A process according to claim 2, wherein the catalyst comprises platinum in an amount of 0.2 to 1.5% by weight of the catalyst, in addition to rhodium.

6. A process according to claim 1, wherein the group $I_B$ metal of the catalyst is copper or silver and the alkali metal of the catalyst is potassium.

7. A process according to claim 1, wherein the catalyst comprises, by weight, 0.25 to 0.65% of rhodium, 0.1 to 0.9% of copper, 0.5 to 3% of potassium and an alumina carrier of specific surface higher than 80 m²/g.

8. A process according to claim 1, wherein the catalyst comprises, by weight, 0.2 to 0.65% of rhodium, 0.1 to 0.9% of at least one metal selected from the group formed of ruthenium, palladium and platinum, 0.1 to 1.9% of copper, 0.5 to 3% of potassium and an alumina carrier of specific surface higher than 80 m²/g.

9. A process according to claim 1, for the dealkylation of toluene to benzene in the presence of water.

10. A process according to claim 1, for the dealkylation, in the presence of water, of alkylaromatic hydrocarbons issued from the catalytic reforming effluents or the effluents of aromatic hydrocarbon production.

* * * * *